(12) United States Patent
Grompone et al.

(10) Patent No.: US 9,056,123 B2
(45) Date of Patent: Jun. 16, 2015

(54) LACTOBACILLI WITH ANTI-OXIDANT ACTION

(75) Inventors: Gianfranco Grompone, Paris (FR); Marie-Christine Degivry, Le Plessis Robinson (FR); Sophie Legrain-Raspaud, Limours (FR); Isabelle Chambaud, Issy les Moulineaux (FR); Raphaëlle Bourdet-Sicard, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 30 days.

(21) Appl. No.: 13/520,456

(22) PCT Filed: Jan. 8, 2010

(86) PCT No.: PCT/IB2010/000194
§ 371 (c)(1),
(2), (4) Date: Nov. 19, 2012

(87) PCT Pub. No.: WO2011/083354
PCT Pub. Date: Jul. 14, 2011

(65) Prior Publication Data
US 2013/0171117 A1    Jul. 4, 2013

(51) Int. Cl.
| | | |
|---|---|---|
| *C12R 1/225* | (2006.01) | |
| *C12N 1/20* | (2006.01) | |
| *A23C 9/12* | (2006.01) | |
| *A61K 35/74* | (2006.01) | |
| *C12R 1/245* | (2006.01) | |

(52) U.S. Cl.
CPC ............... *A61K 35/747* (2013.01); *A61K 35/74* (2013.01); *C12R 1/225* (2013.01); *C12R 1/245* (2013.01); *C12N 1/20* (2013.01)

(58) Field of Classification Search
CPC ......... A23C 9/1234; C12N 1/20; C12R 1/225
See application file for complete search history.

(56) References Cited

U.S. PATENT DOCUMENTS

| | | | |
|---|---|---|---|
| 2004/0029127 A1* | 2/2004 | Postaire et al. | 435/6 |
| 2006/0210668 A1* | 9/2006 | Thorsoe et al. | 426/42 |
| 2011/0059058 A1* | 3/2011 | Chambaud et al. | 424/93.45 |

FOREIGN PATENT DOCUMENTS

| | | |
|---|---|---|
| EP | 0794707 | 9/1997 |
| WO | WO 2009037136 A2 * | 3/2009 |
| WO | 2009/122042 | 10/2009 |

OTHER PUBLICATIONS

Uskova, Antioxidant Properties of Lactic Acid Bacteria—Probiotic and Yogurt Strains, Voprosy Pitaniya, 78, pp. 18-23, 2009.
Giralt, Effects of Probiotic *Lactobacillus casei* DN-114 001 In Prevention of Radiation-Induced Diarrhea: Results from Multicenter, Randomized Placebo-Controlled Nutritional Trial, International Journal of Radiation: Oncology Biology Physics, 71, pp. 1213-1219, 2008.
Ikeda, Influence of Lactic Acid Bacteria on Longevity of *Caenorhabditis elegans* and host Defense Against *Salmonella enterica* Serovar Enteritidis, Applied and Environmental Microbiology, 73, pp. 6404-6409, 2007.
Fabian, The Effect of Daily Consumption of Probiotic and Conventional Yoghurt on Oxidant and Anti-Oxidant Parameters in Plasma of Young Healthy Woman, International Journal for Vitamin and Nutrition Research, 77, pp. 79-88, 2007.
Paik, Effects of *Bacillus* Polyfermenticus SCD on Lipid and Antioxidant Metabolisms in Rats Fed a High-Fat and High-Cholesterol Diet, Biological & Pharmaceutical Bulletin, 28, pp. 1270-1274, 2005.
Kullisaar, Two Antioxidative *Lactobacilli* Strains as Promising Probiotics, International Journal of Food Microbiology, 72, pp. 215-224, 2002.

* cited by examiner

*Primary Examiner* — Jon P Weber
*Assistant Examiner* — Charles Zoltan Constantine
(74) *Attorney, Agent, or Firm* — Morgan, Lewis & Bockius LLP

(57) ABSTRACT

The present invention relates to specific *Lactobacillus* strains with an anti-oxidant effect.

19 Claims, No Drawings

LACTOBACILLI WITH ANTI-OXIDANT ACTION

RELATED APPLICATIONS

The present application is a U.S. National Phase Application of International Application No. PCT/IB2010/000194 (filed Jan. 8, 2010) which is hereby incorporated by reference in its entirety.

FIELD

The present invention is in the field of compositions comprising probiotic bacteria for use in prevention or treatment of oxidative stress.

BACKGROUND ART

All living subjects maintain a reducing environment within their cells. However, due to the aerobic metabolism by the mitochondria and other factors reactive oxygen-derived species such as peroxides and free oxygen radicals are produced. The reducing environment is preserved by enzymes such as superoxide dismutase, catalase and glutathion peroxidase. If the normal redox state is disturbed, the reactive oxygen species may damage all components of the cell, including protein, lipids and especially DNA. This imbalance between the production of reactive oxygen species and the ability to detoxify the reactive intermediates or repair the damage caused by the reactive oxygen species is called oxidative stress.

In humans, oxidative stress is an important factor in aging and degenerative diseases associated with aging such as cancer, arthritis, diabetes, atherosclerosis, Lou Gehrig's disease, Parkinson's disease, heart failure, Alzheimers's disease, and Huntington's disease. The free-radical theory of aging states that organisms age because cells accumulate damage caused by reactive oxygen species over time.

A few strains of lactic acid bacteria with antioxidant properties are known in the art. For instance, U.S. Pat. No. 6,884,415 disclose an antioxidant food product produced by fermenting a food product containing a *L. plantarum* strain having Mn-catalase activity, in the presence of a manganese-containing natural material. The antioxidant properties of this strain depend on the presence of manganese. WO 03/002131 discloses a *L. fermentum* strain (ME-3) and its use as an anti-oxidative probiotic. WO 00/20013 discloses the use of *Lactobacillus* or *Propionibacterium* strains giving rise to increased amounts of propionic acid in the gut for reduction of the level of oxidative stress factors such as IL-6, reactive oxygen species and adhesion molecules. A preferred strain disclosed in this document is *Lactobacillus plantarum* 299v.

Ikeda et al, (2007, AEM 73:6404-6409) compared the lifespan and *Salmonella* resistance of *C. elegans* worms fed with lactic acid bacteria (lactobacilli and bifidobacteria) with those of worms fed *Escherichia coli* OP50 (the standard food for *C. elegans*). They report that all the lactobacilli or bifidobacteria tested have a similar effect in increasing the life-span and *Salmonella* resistance when compared to *E. coli* OP50. However, the effect of lactic acid bacteria on worms submitted to oxidative stress was not assessed.

SUMMARY OF THE INVENTION

The inventors have tested the effect of lactic acid bacteria on *C. elegans* submitted to oxidative stress, compared to the control *E. coli* feed. They found that, in contrast with what was observed by Ikeda et al. concerning life span, only very few specific strains of *Lactobacillus* prevented the damaging effects of this imposed oxidative stress.

The present invention therefore provides *Lactobacillus* strains selected by the inventors on the basis of their ability to alleviate the effects on *C. elegans* of oxidative stress induced by hydrogen peroxide ($H_2O_2$), for use as anti-oxidant when administered in vivo to a subject, and therefore for treating, alleviating, or preventing oxidative stress-related conditions or clinical manifestations.

The *Lactobacillus* strains identified by the inventors are particularly suitable for preparing anti-oxidant compositions to be administered especially in the form of food or dietary supplementation, to mammals, in particular humans, exposed to oxidative stress, such as elderly, shift workers, students during exam periods, firemen, subjects exposed to radiations or to air pollution. Especially the elderly are an appropriate target group, since the aged gut and the immunosenescence is prone to less effective resistance to the oxidative stress and production of ROS. The *Lactobacillus* strains of the present invention are therefore particularly suitable to improve life quality in elderly by nutritional intervention.

DETAILED DESCRIPTION OF THE INVENTION

*Lactobacillus* Strains.

The three specific *Lactobacillus* strains selected by the inventors are described below:

The first strain is the *Lactobacillus casei* strain DN 114 001, which was deposited according to the Budapest Treaty at the CNCM (Collection Nationale de Cultures de Microorganismes, 25 Rue du Docteur Roux, Paris) on Dec. 30, 1994 with the number I-1518. Detailed characteristics of this strain are disclosed in PCT application WO 96/20607.

The second strain is the *Lactobacillus rhamnosus* strain DN 116 010 which was deposited according to the Budapest Treaty at the CNCM on Nov. 19, 2006 with the number I-3690. Detailed characteristics of this strain are disclosed in PCT application WO 2009/122042.

A third strain is the *Lactobacillus rhamnosus* strain DN 116 063 which was deposited according to the Budapest Treaty at the CNCM on Dec. 16, 2009 with the number I-4271. This strain was identified as belonging to *L. rhamnosus* on the basis of both PCR typing and biochemical activity on API 50 CHL kit (Biomerieux, france). According to the Api 50CHL results the I-4271 strain ferments the following sugars and alcohols: Ribose, galactose, D-glucose, D-fructose, D-mannose, L-sorbose, rhamnose, mannitol, sorbitol, Methyl-D glucoside, N-acetylglucosamine, amygdalin, arbutine, esculine, salicine, cellulose, maltose, lactose, saccharose, trehalose, melezitose, beta-gentiobiose, D-turanose, D-tagatose, gluconate.

The present invention also encompasses the use of mutant strains or genetically transformed strains derived from any one of the parent strains CNM I-1518, I-3690 and I-4271, and still having anti-oxidant activity (i.e. being able to alleviate the effects on *C. elegans* of oxidative stress induced by $H_2O_2$), for anti-oxidant purposes. These mutant or genetically transformed strains can be strains wherein one or more endogenous gene(s) of the parent strain has (have) been mutated, for instance to modify some of its metabolic properties (e.g. its ability to ferment sugars, its resistance to acidity, its survival to transport in the gastrointestinal tract, its post-acidification or its metabolite production). They can also be strains resulting from the genetic transformation of the parent strain by one or more gene(s) of interest, for instance in order to give to said strain additional physiological features, or to allow it to express proteins of therapeutic or vaccinal interest that one wishes to administer through said strains.

The present invention also encompasses the new strain I-4271, as well as mutant or genetically transformed strains derived thereof as described above. Preferably, these mutants or genetically transformed cells still have the anti-oxidant ability of strain I-4271.

Compositions:

The invention also encompasses compositions comprising one or more of the *Lactobacillus* strains CNCM I-1518, I-3690 and I-4271, or mutant or genetically transformed strains derived thereof; for use as antioxidant when administered in vivo to a subject.

In the compositions of the invention, said *Lactobacillus* strains can be used in the form of whole bacteria which may be living or not. Alternatively, they can be used in the form of a bacterial lysate or in the form of bacterial fractions; the bacterial fractions suitable for this use can be chosen, for example, by testing their properties of alleviating the effects on *C. elegans* of oxidative stress induced by hydrogen peroxide ($H_2O_2$).

The compositions of the invention can be in any form suitable for administration, in particular oral administration. This includes for instance solids, semi-solids, liquids, and powders. Liquid composition are generally preferred for easier administration, for instance as drinks.

When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Examples of the compositions of the invention are nutritional compositions, including food products and in particular dairy products. The administration in the form of a fermented dairy product has the additional advantage of providing a food product with low redox potential which is not only advantageous for the growth or survival of the *Lactobacillus* strains but also for the further treatment and/or prevention of oxidative stress in human subjects consuming the product.

Nutritional compositions of the invention also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

Other examples of compositions of the invention are pharmaceutical or cosmetic compositions.

The compositions of the invention can also comprise one or more other strain(s) of lactic acid bacteria, probiotic or not, for instance one or more bacterial strain(s) selected from the genera *Lactobacillus, Lactococcus, Streptococcus*, and *Bifidobacteria*. In particular, this (these) other strains(s) can include one or more strain(s) of *Streptococcus thermophilus*, and/or one or more strain(s) of *Lactobacillus bulgaricus*.

Application

The *Lactobacillus* strains and compositions of the present invention are useful to protect against oxidative stress and/or to prevent the damage exerted by oxidative stress. They can therefore be used as antioxidant to be administered for treating or preventing diseases involving oxidative stress.

They are preferably administered to humans, in particular humans suffering from oxidative stress, more preferably elderly, and shift workers, students during exam periods, firemen, and subjects exposed to radiations and/or to air pollution.

The present invention thus provides a method for treating, alleviating, or preventing an oxidative stress-related condition in a subject in need thereof, wherein said method comprises administrating to said subject a *Lactobacillus* strain or composition of the invention.

Especially the elderly are an appropriate target group, since the aged gut and the immunosenescence is prone to less effective resistance to the oxidative stress and production of ROS. Oxidative stress is also an important factor in aging: the free-radical theory of aging states that organisms age because cells accumulate damage caused by reactive oxygen species over time. The *Lactobacillus* strains of the present invention are therefore particularly suitable to improve life quality in elderly by nutritional intervention. An elderly person is a person having an age of 55 years or more, in particular of the age of 65 or more.

In humans, oxidative stress is also an important etiologic factor in degenerative diseases such as cancer, arthritis, diabetes, artherosclerosis, Lou Gehrig's disease, Parkinson's disease, heart failure, Alzheimers's disease, and Huntington's disease. Therefore, the strains and compositions of the present invention are advantageously administered to human subjects suffering from and/or at risk of a disease selected from the group consisting of cancer, arthritis, diabetes, artherosclerosis, Lou Gehrig's disease, Parkinson's disease, heart failure, Alzheimers's disease, and Huntington's disease.

EXAMPLE 1

Effect of Lactic Acid Bacteria on Survival of *C. Elegans* with or without Oxidative Stress in Liquid Media Experiments have been carried out with a *C. elegans* mutant strain (BA17 fem-1(hc17) which is not fertile at 25° C., but retains the life span characteristics of wild-type. BA17 worms were synchronized by isolating eggs from gravid adults at 20° C., hatching the eggs overnight in M9 medium (10 vol % MRS, fluorodexouridine 110 ug/ml) plus 5 ug/ml cholesterol and isolating $L_1$-stage worms in the wells of a microtiter plate. The worms were grown without agitation during three days at 25° C. and 80-85% relative humidity. These larvae were transferred to a plate comprising M9 medium plus cholesterol and incubated for 3 days at 25° C. 80-85% humidity while undergoing control or experimental feeding. At least 50 worm were present per well.

After 3 days, when the worms had reached adult stage, oxidative stress was applied by addition of hydrogen peroxide ($H_2O_2$) at a concentration of 5 mM. As a control no $H_2O_2$ was used. Anti-oxidant resistance was read out as viability, assessed after 5 h by microscopy. Worms were incubated in these conditions during 5 hours. To score for antioxidant capacity the worms were consider to be dead (stressed) if they were paralyzed.

The worms were fed with $4*10^6$ cfu/ml of the standard feed *E. coli* OP50, or of different strains of lactic acid bacteria belonging to the genera *Bifidobacterium, Lactobacillus* or *Streptococcus*. Kanamycin, 30 μg/ml, was added to prevent growth of *E coli* OP50 or of the tested lactic acid bacteria during the assay.

Survival in Absence of Oxidative Stress

In the absence of oxidative stress during the incubation time the viability of worms fed with *E. coli* varied between 100 to about 90%. The lactic acid bacteria gave similar or better survival rates, which is indicative for a similar or improved longevity, as shown in Table 1 for some of the tested strains.

TABLE 1

Effect of lactic acid bacteria feed on longevity of *C. elegans*.

| Strain - Species | Viability % |
| --- | --- |
| S2A - *S. thermophilus* | 95.7 |
| S1B - *S. thermophilus* | 98.0 |
| S2B - *S. thermophilus* | 94.1 |
| S1C - *S. thermophilus* | 94.5 |
| S1D - *S. thermophilus* | 98.2 |
| S1E - *S. thermophilus* | 100.0 |
| S1F - *S. thermophilus* | 95. |
| S1G - *S. thermophilus* | 98.2 |
| S1H - *S. thermophilus* | 97.1 |
| L2A - *L. acidophilus* | 91.9 |
| L5A - *L. casei* | 100 |
| L6A - *L. delbrueckii* | 94.1 |
| L8A - *L. johnsoni* | 96.0 |
| L9A - *L.. plantarum* | 91.75 |
| OP50 | 89.5 |

This is in accordance with the finding of Ikeda et al. (2007, cited above).

Survival Under Oxidative Stress

The effect of 99 strains of lactic acid bacteria on survival under oxidative stress was tested with 2, 3 and 5 mM $H_2O_2$. In the presence of 5 mM $H_2O_2$ the viability in the presence of *E. coli* OP50 was about 93% compared to the absence of stress. This is indicative for a 93% protection against oxidative stress. Table 2 below shows the effect of selected lactic acid bacteria on protection against oxidative stress, with the protective effect exerted by the control *E. coli* OP50 set at 100% as a reference level.

TABLE 2

Level of protection against 5 mM $H_2O_2$ oxidative stress, conferred by lactic acid bacteria compared to *E. coli* OP50.

| Strain - Species- | Level of protection % |
| --- | --- |
| *E. coli* OP50 | 100 |
| Lactobacilli | |
| L8F *L. plantarum* (299v) | 14.6 |
| L9F *L. rhamnosus* (LGG) | 21.6 |
| L10F *L. rhamnosus* | 9.7 |
| L1G *L. acidophilus* | 102.5 |
| L3G *L. casei* | 7 |
| L4G - *L. casei* | 30 |
| L6G - *L. fermentum* | 23 |
| L7G - *L. helveticus* | 95 |
| L8G - *L. plantarum* | 18 |
| L9G - *L rhamnosus* (HN001) | 81 |
| L10G - *L. rhamnosus* | 77 |
| L1H - *L. amylovorus* | 70 |
| L4H - *L. casei* | 87 |
| L5H - *L. delbrueckii* | 6 |
| L7H - *L. johnsonii* | 3 |
| L8H - *L. plantarum* | 9 |
| L10H - *L. rhamnosus* | 8 |
| L8B - *L. johnsonii* | 76.8 |
| L9A - *L. plantarum* | 18.7 |
| L9B - *L. plantarum* | 13.3 |
| L10B - *L. rhamnosus* | 5.2 |
| L11B - *L. rhamnosus* | 70.9 |
| L2C - *L. delbrueckii* | 15.7 |
| L4C - *L. brevis* | 12.8 |
| L6C - *L. delbrueckii* | 0.0 |
| L8C - *L. johnsonii* | 59.3 |
| L10C - *L. rhamnosus* | 105 |
| L11C - *L. rhamnosus* | 96.3 |
| L4D - *L. casei* | 7.5 |
| L6B - *L. delbrueckii* | 21.2 |
| L8B - *L. johnsonii* | 82.2 |
| L5C - *L. casei* | 4.1 |
| L7C - *Lactobacillus* sp. | 5.7 |
| L2D - *L. bulgaricus* | 0.0 |
| L5D - *L. casei* | 0.0 |
| L2E - *L. bulgaricus* | 0.0 |
| L3F - *L. casei* | 0.0 |
| L4F - *L. casei* | 85.1 |
| L6F - *L. fermentum* | 0.0 |
| L7F - *L. helveticus* | 11.0 |
| L11A - *L. rhamnosus* | 102 |
| L4B - *L. casei* | 109 |
| L3B - *L. bulgaricus* | 80.1 |
| L6A - *L. delbrueckii* | 26.3 |
| L2A - *L. acidophilus* | 100 |
| L2B - *L. brevis* | 16.0 |
| L5A - *L. casei* | 9.8 |
| L7B - *L. fermentum* | 0.0 |
| L5B - *L. casei* | 89.6 |
| L8A - *L. johnsonii* | 111 |
| L8D - *L. johnsonii* | 87.1 |
| L9D - *L. reuteri* | 91.6 |
| L10D - *L. rhamnosus* | 94.1 |
| L11D - *L. rhamnosus* | 100 |
| L3E - *L. casei* | 104 |
| L4E - *L. casei* | 59.4 |
| L5E - *L. delbrueckii* | 34.2 |
| L6E - *L. fermentum* | 56.7 |
| L8E - *L. pentosus* | 54.2 |
| L9E - *L. gasseri* | 58.1 |
| L10E - *L. rhamnosus* | 88.6 |
| L1F - *Lactobacillus* sp. | 87.5 |
| L2F - *L. bulgaricus* | 52.2 |
| L3A - *Lactobacillus* sp. | 3 |
| L1B - *L. acidophilus* | 1 |
| Bifidobacteria | |
| B1B - *B.. animalis* | 35.8 |
| B1C - *B.. animalis* | 26.2 |
| B1D - *B.. animalis* | 7.4 |
| B1E - *B.. animalis* | 0.0 |
| B1G - *B. bifidum* | 9.0 |
| B2G - *B.. longum* | 5.9 |
| Streptococci | |
| S2A - *S. thermophilus* - | 84.3 |
| S1B - *S. thermophilus* | 61.5 |
| S2B - *S. thermophilus* | 85.0 |
| S1C - *S. thermophilus* | 45.8 |
| S1D - *S. thermophilus* | 93.8 |
| S1E - *S. thermophilus* | 89.7 |
| S1F - *S. thermophilus* | 8.2 |
| S1G - *S. thermophilus* | 11.7 |
| S1H - *S. thermophilus* | 42.3 |

From Table 2 above it can be concluded that *Bifidobacterium* strains did not confer resistance to oxidative stress and that surprisingly only very few strain of *Streptococcus* and *Lactobacillus* were able to confer resistance to oxidative stress at a level higher than that of the control strain. The strains improving viability in the absence of oxidative stress were not necessarily the strains also giving the best protection against oxidative stress. This indicates that the improved effect of lactic acid bacteria on viability does not appear to be correlated to an effect on oxidative stress. These results also show that the anti-oxidative effect is strongly strain specific, and that in fact only very few strains of *Streptococcus* and *Lactobacillus* have the ability to reduce the effects of oxidative stress in vivo.

EXAMPLE 2

Effect of Selected Strains of Lactic Acid Bacteria on Resistance Against Oxidative Stress of Wild Type *C. Elegans* Grown on Agar Plates Wild type *C. elegans* (N2) were grown on NG agar plates for 5 days with lanes of *E coli* OP50 or with lanes of selected strains of lactic acid bacteria from example 1 and incubated with 3 mM $H_2O_2$ for 5 h. The viability was assessed just before and after the 5 h incubation and the % survival under oxidative stress was determined by determining the % worms that died during the incubation time. The results are shown in Table 3. Also in an assay with agar plates instead of wells specific strains of lactic acid bacteria were shown to exert a protective effect against oxidative stress, but not all strains tested in example 1 turned out to be effective. Of the 99 strains, 3 *Lactobacillus* strains, 10C, 11D and 3E were effective. Strain 10C is *Lactobacillus rhamnosus* DN 116 063 (CNCM I-4271), strain 11D is *Lactobacillus rhamnosus* DN 116 010 (CNCM 13690) and strain 3E is *Lactobacillus casei* DN 114 001 (CNCM-1518)

None of the *Streptococcus* strain tested (S2B, S1E and S1D) was able to protect against oxidative stress at a level above *E. coli* OP50.

TABLE 3

Level of protection against 5 mM $H_2O_2$ oxidative stress, conferred of lactic acid bacteria relative to the protection conferred by *E. coli* OP50 on agar plates.

| Strain - species | Protection against oxidative stress, % relative to *E. coli* OP50 |
|---|---|
| L10C - *L. rhamnosus* | 162 |
| L11D - *L. rhamnosus* | 162 |
| L3E - *L. casei* | 106 |
| L11C - *L. rhamnosus* | 57 |
| L4B - *L. casei* | 69 |
| L8A - *L. johnsonii* | 0 |
| S1D - *S. thermophilus* | 38 |
| S1E - *S. thermophilus* | 49 |

EXAMPLE 3

Fermented Dairy Product

A concentrated freeze dried preparation of *Lactobacillus rhamnosus* CNCM I-4271 was prepared as known in the art. A drink yoghurt was prepared as known in the art by fermenting milk. At the end of the production of the drink yogurt *L. rhamnosus* CNCM I-4271 was added to a final concentration of about $5.10^8$ cfu/ml. The product was stored at about 7° C.

The invention claimed is:

1. A composition comprising an isolated *Lactobacillus* strain deposited with the Collection Nationale de Cultures de Microorganismes (CNCM) under Accession No. I-4271,
   wherein the composition is yogurt, and
   said strain is able to alleviate the effects on *Caenorhabditis elegans* of oxidative stress induced by hydrogen peroxide.

2. The composition of claim 1 further comprising a food supplement.

3. The composition of claim 1, wherein the composition is a yogurt drink.

4. The composition of claim 1, wherein the composition comprises $10^5$ to $10^{13}$ cfu per g dry weight of the living strain CNCM I-4271.

5. The composition of claim 1, wherein the composition comprises $10^4$ to $10^{12}$ cfu per g dry weight of the living strain CNCM I-4271.

6. The composition of claim 1, further comprising a strain of *Streptococcus thermophilus*.

7. The composition of claim 1, further comprising a strain of *Lactobacillus bulgaricus*.

8. The composition of claim 1, further comprising strains of *Streptococcus thermophilus* and *Lactobacillus bulgaricus*.

9. The composition of claim 1, further comprising milk.

10. A method of treating, or alleviating an oxidative stress from an oxidative stress condition in a subject comprising administering a composition of claim 1.

11. The method of claim 10 wherein the subject is selected from elderly, shift workers, students during exam periods, firemen, subjects exposed to radiation and/or to air pollution.

12. The method of claim 10 wherein the oxidative stress-condition is selected from the group consisting of cancer, arthritis, diabetes, atherosclerosis, Lou Gehrig's disease, Parkinson's disease, heart failure, Alzheimer's disease, and Huntington's disease.

13. The method of claim 10, wherein the composition comprises $10^5$ to $10^{13}$ cfu per g dry weight.

14. The method of claim 10, wherein the composition is a yogurt drink.

15. The method of claim 10, wherein the composition comprises $10^5$ to $10^{13}$ cfu per g dry weight of the living strain CNCM I-4271.

16. The method of claim 10, wherein the composition comprises $10^4$ to $10^{12}$ cfu per g dry weight of the living strain CNCM I-4271.

17. The method of claim 10, wherein the composition further comprises a strain of *Streptococcus thermophilus*.

18. The method of claim 10, wherein the composition further comprises a strain of *Lactobacillus bulgaricus*.

19. The method of claim 10, wherein the composition further comprises strains of *Streptococcus thermophilus* and *Lactobacillus bulgaricus*.

* * * * *